(12) United States Patent
Hopkins

(10) Patent No.: US 9,974,559 B2
(45) Date of Patent: May 22, 2018

(54) CUTTING GUIDE WIRE AND METHOD OF USE THEREOF

(71) Applicant: COOK MEDICAL TECHNOLOGIES LLC, Bloomington, IN (US)

(72) Inventor: Marie Hopkins, Cleveland Heights, OH (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 405 days.

(21) Appl. No.: 14/921,119

(22) Filed: Oct. 23, 2015

(65) Prior Publication Data

US 2016/0157879 A1    Jun. 9, 2016

Related U.S. Application Data

(60) Provisional application No. 62/087,331, filed on Dec. 4, 2014.

(51) Int. Cl.

| | | |
|---|---|---|
| *A61B 17/3207* | (2006.01) | |
| *A61F 2/844* | (2013.01) | |
| *A61F 2/958* | (2013.01) | |
| *A61M 25/01* | (2006.01) | |
| *A61B 17/00* | (2006.01) | |

(Continued)

(52) U.S. Cl.
CPC .......... *A61B 17/3207* (2013.01); *A61F 2/844* (2013.01); *A61F 2/958* (2013.01); *A61B 2017/00327* (2013.01); *A61B 2017/22042* (2013.01); *A61B 2017/22044* (2013.01); *A61B 2017/22095* (2013.01); *A61B 2017/320733* (2013.01); *A61F 2250/0067* (2013.01); *A61M 25/0147* (2013.01); *A61M 2025/09175* (2013.01)

(58) Field of Classification Search
CPC ............ A61B 2017/22042–2017/2044; A61B 2017/22094–2017/22095; A61B 2017/320733; A61B 2017/320741; A61M 25/09; A61M 2025/09175–2025/09183
See application file for complete search history.

(56) References Cited

U.S. PATENT DOCUMENTS 4,548,206 A * 10/1985 Osborne ......... A61M 25/09025
                                                  600/585
5,234,003 A *  8/1993 Hall .................. A61M 25/09
                                                  600/434

(Continued)

OTHER PUBLICATIONS

Extended Search Report in corresponding European Application No. 15197387.2, dated Apr. 18, 2016, 5 pages.

*Primary Examiner* — Shaun L David
(74) *Attorney, Agent, or Firm* — Brinks Gilson & Lione

(57) ABSTRACT

The present invention generally relates to a wire guide for use in procedures within a body vessel and to methods of using such devices. One embodiment of the wire guide includes a helically wound coil having its distal end closed with a cap and having a deflection wire housed within. The deflection wire simultaneously acts to deflect the distal end of the helically wound coil in a direction perpendicular to the longitudinal movement axis of the wire guide while moving a first blade attaching to a distal portion of the deflection wire from a retracted position to an extended position.

20 Claims, 6 Drawing Sheets

(51) Int. Cl.
  *A61B 17/22*   (2006.01)
  *A61M 25/09*   (2006.01)

(56) References Cited

U.S. PATENT DOCUMENTS

| | | | |
|---|---|---|---|
| 5,308,324 A | 5/1994 | Hammerslag et al. | |
| 6,231,546 B1* | 5/2001 | Milo | A61B 17/3207 600/585 |
| 6,824,550 B1* | 11/2004 | Noriega | A61B 17/320758 604/22 |
| 7,713,215 B2 | 5/2010 | Shriver | |
| 2001/0000041 A1* | 3/2001 | Selmon | A61B 17/3207 600/585 |
| 2002/0019644 A1* | 2/2002 | Hastings | A61B 17/22 606/159 |
| 2002/0032391 A1* | 3/2002 | McFann | A61B 17/221 600/585 |
| 2005/0171478 A1* | 8/2005 | Selmon | A61B 17/3207 604/164.01 |
| 2006/0074442 A1* | 4/2006 | Noriega | A61B 17/32002 606/159 |
| 2007/0100257 A1* | 5/2007 | Melsheimer | A61M 25/09 600/585 |
| 2007/0213689 A1 | 9/2007 | Grewe et al. | |
| 2007/0219464 A1* | 9/2007 | Davis | A61M 25/0138 600/585 |
| 2008/0221601 A1* | 9/2008 | Huynh | A61B 17/320758 606/159 |
| 2009/0198153 A1* | 8/2009 | Shriver | A61B 17/00234 600/585 |
| 2010/0063534 A1 | 3/2010 | Kugler et al. | |
| 2012/0265229 A1 | 10/2012 | Rottenberg et al. | |
| 2013/0238003 A1 | 9/2013 | Fischer et al. | |
| 2013/0289392 A1 | 10/2013 | Patel et al. | |
| 2013/0304108 A1 | 11/2013 | Weber et al. | |
| 2014/0180323 A1 | 6/2014 | Shriver | |
| 2014/0350568 A1* | 11/2014 | Shekalim | A61M 25/09 606/127 |

* cited by examiner

CUTTING GUIDE WIRE AND METHOD OF USE THEREOF

RELATED APPLICATIONS

This patent application claims the benefit of U.S. provisional patent application No. 62/087,331, filed Dec. 4, 2014, the entire contents of which application is hereby incorporated by reference.

TECHNICAL FIELD

The present invention generally relates to a wire guide for use in percutaneous procedures within a body cavity and to methods of using such devices. One embodiment of the wire guide includes a helically wound coil having its distal end closed with a cap and having a deflection wire housed within. Translation of the deflection wire simultaneously acts to deflect the distal end of the helically wound coil in a direction perpendicular to the longitudinal movement axis of the wire guide while moving a first blade attaching to a distal portion of the deflection wire from a retracted position to an extended position.

BACKGROUND

Wire guides are commonly used in procedures, such as angioplasty procedures, diagnostic and interventional procedures, percutaneous access procedures and radiological and neuroradiological procedures in general, to introduce a wide variety of medical devices into the vascular system or into other vessels of a human or veterinary patient. For example, wire guides are used for advancing intraluminal devices such as stent delivery catheters, balloon dilation catheters, atherectomy catheters, and the like within body lumens.

Typically, the wire guide is positioned inside the inner lumen of an introducer catheter. The wire guide is advanced out of the distal end of the introducer catheter into the patient until the distal end of the wire guide reaches the location where the interventional procedure is to be performed. After the wire guide is inserted, another device such as a stent and stent delivery catheter is advanced over the previously introduced wire guide into the patient until the stent delivery catheter is in the desired location. After the stent has been delivered, the stent delivery catheter can then be removed from a patient by retracting the stent delivery catheter back over the wire guide. The wire guide may be left in place after the procedure is completed to ensure easy access if this is required.

Peripheral chronic total occlusion ("CTO") is a condition where an obstruction has built up in a peripheral vessel to the extent where there is no blood flow through the vessel. This blockage can lead to ischemic conditions in the extremities and commonly results in the need for invasive treatment. In these CTOs it is common for there to be a cholesterol crystal covering at each end of the occlusion. This covering exists due to macrophages accumulated in an inflammatory response and an increase in retained low-density lipoprotein LDL.

An occlusion may also result from thrombosis. Thrombosis is the formation of a thrombus, or blood clot, within the vascular system of a patient. A blood clot typically occurs when blood hardens from a liquid to a solid. When attached to vessel walls, blood clots, and other substances, such as plaque or fat, may reduce or block blood flow downstream from the clot.

The resulting blockage may prevent critical blood flow and oxygen from reaching certain tissues and, thus, may result in damage to the tissues. Regardless of the particular location of the occlusion within the vascular system, such an occlusion or, in particular, a CTO, if left untreated, may cause serious damage and, in some cases, may become life threatening.

A number of invasive and non-invasive techniques are available for treating an occlusion. These include exercise, open surgery and pharmacological methods. For example, some percutaneous techniques include the use of pharmacological agents, also referred to as thrombolytic agents, to help dissolve clots. Other percutaneous techniques may include the use of a wire guide and/or catheter to cross the occlusion and recanalize the vessel. However, crossing a CTO using a wire guide and/or catheter may be difficult and, sometimes, impossible, due to the hardness of the clot or other occlusion.

In such situations, the sub-intimal tracking and re-entry (STAR) technique allows for a bypass of the occlusion by entering the subintimal layer just before the occlusion and exiting once past the occlusion, and then stenting or ballooning open the burrowed path in the subintimal space and provide a path for blood to flow.

BRIEF SUMMARY

One aspect of the present invention provides a wire guide including a helically wound coil having a proximal end, a closed distal end and a longitudinal movement axis, where the distal end of the helically wound coil is closed with a cap. A first deflection wire is housed within the helically wound coil and is responsive to a translational displacement on the longitudinal movement axis in a distal direction to deflect the distal end of the helically wound coil in a direction on an axis perpendicular to the longitudinal movement axis of the helically wound coil while simultaneously moving a first blade attached to the distal portion of the first deflection wire from a retracted position to an extended position.

The guide wire may also include a second deflection wire housed within the helically wound coil. A distal end of the second deflection wire may attach to the distal end of the first deflection wire. The second deflection wire, responsive to a translational displacement on the longitudinal movement axis, simultaneously deflects the distal end of the helically wound coil in a second direction, the second direction being opposite the first direction and on an axis perpendicular to the longitudinal movement axis of the helically wound coil, while moving a second blade attached to a distal end of the second deflection wire from a retracted position to an extended position.

In certain embodiments, the guide wire also includes a stability sheath positioned between the deflection wires and the helically wound coil. The guide wire may also include at least one radiopaque marker. In other embodiments, the guide wire includes a lubricious polymer coating surrounding the helically wound coil.

In another embodiment the guide wire includes a helically wound coil, where the coils at the distal end are in a more relaxed state than the coils at the proximal end. A cap is secured to the distal end of the helically wound coil. A first deflection wire and a second deflection wire disposed within the helically wound coil and secured together at the distal end of the helically wound coil. The first deflection wire runs from the proximal end to the distal end of the helically wound coil. A first blade is secured near the distal end of the first deflection wire and a second blade is secured near the distal end of the second deflection wire. The first blade is housed within the cap when the first deflection wire is in a relaxed state and the first blade extended from the cap when the first deflection wire is in a deflection state, and the second blade housed within the cap when the second deflection wire is in a relaxed position and the second blade extended from the cap when the second deflection wire is in a deflection state.

Another aspect of the present invention provides a method of crossing an occlusion in a lumen of a patient vessel. In one embodiment, the method includes introducing a distal end of a guide wire as disclosed herein into the patient vessel and advancing the distal end of the guide wire to a first side of the occlusion. The first deflection wire is translationally displaced, whereby the distal end of the helically wound coil is deflected and the first blade is extended to contact and cut a wall of the vessel.

The distal end of the guide wire is advanced to enter a subintimal layer of the wall and through the subintimal region, in a direction substantially aligned with a path of the vessel, to position the distal end of the guide wire adjacent to a region of the vessel beyond the obstruction. The first deflection wire or the second deflection wire is translationally displaced, whereby the distal end of the helically wound coil is deflected to re-enter the lumen of the vessel at a second side of the obstruction. In one embodiment the vessel is a vascular vessel. In another embodiment, the obstruction is a result of thrombosis.

The method may also include advancing a device comprising a balloon catheter over the guide wire and positioning an expandable balloon portion of the balloon catheter within the subintimal region. The balloon is expanded within the subinitimal region, whereby the subinitimal region is expanded. An expandable stent may be positioned on the expandable balloon portion of the balloon catheter.

In another embodiment, the method includes advancing a device including an expandable stent over the guide wire and positioning the expandable stent within the subintimal region. The stent is expanded within the subinitimal region, whereby the subinitimal region is expanded. The stent may be a self-expandable stent or a balloon-expandable stent.

BRIEF DESCRIPTION OF THE DRAWINGS

FIGS. 3 (A) and 3(B) are illustrations showing two embodiments of blades for use with a cutting guide wire.

FIG. 5(A) shows a cap having slits near the circumferential edge of the cap. FIG. 5(B) shows a cap having a plurality of legs.

FIGS. 6 (A) and 6(B) are illustrations showing one embodiment of the interior of the cap portion of one embodiment of a cutting guide wire having a retractable blade.

DETAILED DESCRIPTION

Figure 1:
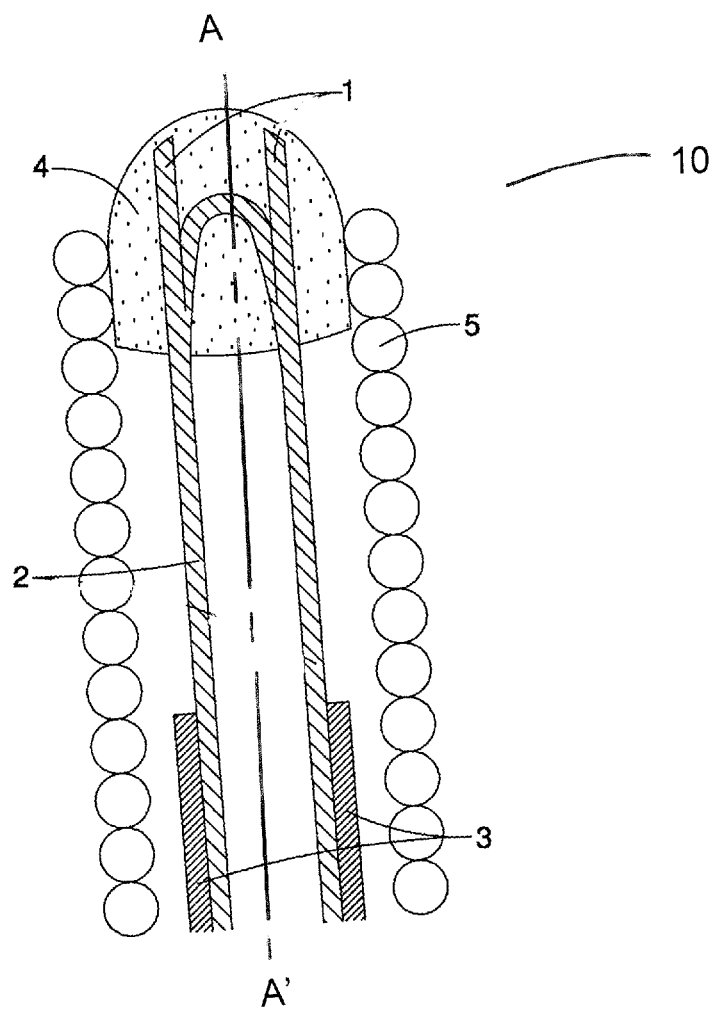
FIG. 1 is an illustration showing a distal portion of one embodiment of a cutting guide wire having a retractable blade.

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. Each disclosed feature or features can be combined with the generalized features discussed herein, to form a disclosed embodiment of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

As used herein the terms "comprise(s)," "include(s)," "having," "has," "can," "contain(s)," and variants thereof, are intended to be open-ended transitional phrases, terms, or words that do not preclude the possibility of additional acts or structures. The present invention also contemplates other embodiments "comprising," "consisting of" and "consisting essentially of," the embodiments or elements presented herein, whether explicitly set forth or not.

As used herein, the terms "proximal" and "distal" should be understood as being in the terms of an operator using the device. The term distal means the portion of the device which is farthest from the operator and the term proximal means the portion of the device which is nearest to the operator. The distal portion of the device is that portion of the device that is inserted into the subject which the proximal portion of the device remains outside the body of the subject.

As used herein, the term "body vessel" means a body passage or lumen, including, but not limited to, vascular coronary or peripheral vessels, esophageal, intestinal, biliary, urethral and ureteral passages.

As used herein, the term patient refers to a human or veterinary subject.

Cutting Guide Wire

One aspect of the present invention provides a cutting guide wire having at least one retractable blade. Various embodiments of such a cutting guide wire will now be disclosed with reference to FIG. 1 and FIGS. 6(A) and (B), which illustrates the distal portion of one embodiment of such a guide wire.

Guide wire 10 includes helically wound coil 5 having a proximal end, a distal end and a longitudinal movement axis A-A'. Closed distal end of helically wound coil 5 is closed with cap 4. First deflection wire 7 is housed within helically wound coil 5 and has a proximal end and a distal end. First deflection wire 7, responsive to a translational displacement on the longitudinal movement axis A-A' in the distal direction, simultaneously acts to deflect the distal end of helically wound coil 5 in a first direction, the direction being on an axis perpendicular to the A-A' axis of helically wound coil 5, while moving first blade 8 attaching to a distal portion of first deflection wire 7 from a retracted position to an extended position. First blade 8 in the retracted position being housed entirely within cap 4 and first blade 8 in the extended position extending distally from cap 4. First deflection wire 8 may extend to the proximal end of the guide wire to allow for manipulation by the user.

In one embodiment, guide wire 10 includes second deflection wire 2 housed within helically wound coil 5 and having its distal end attached to the distal end of first deflection wire 7. Second deflection wire 2, responsive to a translational displacement on the A-A' axis in a distal direction, simultaneously deflects the distal end of helically wound coil 5 in a second direction, the second direction being opposite the first direction and on an axis perpendicular to the A-A' axis of helically wound coil 5, while moving second blade 1 attached to the distal end of second deflection wire 2 from a retracted position to an extended position. When in the retracted position, second blade 1 is housed within cap 4. When in the extended position, second blade 1 extends distally from cap 4. The guide wire can also include stability sheath 3 positioned between the deflection wires and the helically wound coil. In some embodiments, stability sheath 3 extends for the proximal end of the guide wire to just proximal of the distal end of the guide wire. In these embodiments, stability sheath 3 does not reduce the maneuverability of the distal end of the guide wire.

Translational displacement of both first deflection wire 7 and second deflection wire 2 on the A-A' axis in a distal direction simultaneously moves first blade 8 and second blade 1 from their retracted positions to their extended positions. Return of the deflection wires to their relaxed positions will result in retraction of the blades. In those situations where both deflection wires as displaced by the same distance, the distal end of helically wound coil 5 is not deflected from the A-A' axis.

Helically wound coil 5 may be made from, for example, stainless steel, a stainless steel alloy, a nickel-titanium alloy, such as NITINOL, or combinations of these materials. It may be wound from a wire material having a circular, or non-circular, cross sectional shape. The pitch of the coil may be constant throughout its length. Alternatively, the pitch may vary along the length of the coil. For example, the coils at the distal end of the coil may be in a more relaxed state than the coils at the proximal end.

Helically wound coil 5 may be of any desired length and may have any outer diameter, suitable for the intended use of the coil. In some embodiments, helically wound coil 5 may generally be about 90 to about 300 cm, and for use within a patient's coronary system the wire guide is typically about 180 cm in length. In certain embodiments, helically wound coil 5 is between 90 and 400 cm in length. In other embodiments, helically wound coil 5 is between 280 and 400 cm in length. In yet other embodiments, helically wound coil 5 is between 300 and 400 cm in length or is at least 300 cm in length.

In certain embodiments, the guide wire may include a radiopaque material, for example, platinum or gold, to allows for better visibility during manipulation of the guide wire. Such a material may be included, for example, as part of helically wound coil 5 and/or cap 4. For example, a longitudinal radiopaque marker line may be disposed on an exterior surface of helically wound coil 5. Alternatively, or in addition, an echogenic material, such as tungsten, included at these, or other, positions in the guide wire. The guide wire may also include a lubricious polymer coating surrounding helically wound coil 5. Such a coating may assist in the passage of the guide wire through the vessel of the patient. The polymer coating may include a polymer such as, but not limited to, a fluoropolymer, for example, polytetrafluoroethylene, or a polyurethane. The coating may be applied by, for example, dipping, spraying or heat shrinking.

Figure 5A:
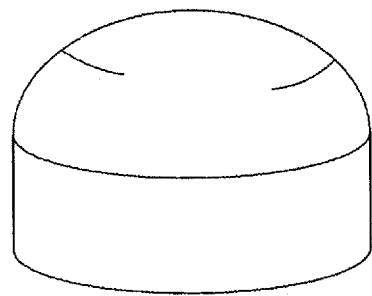
FIGS. 5(A) and 5(B) are illustrations showing two embodiments of the cap portion of a cutting guide wire.
Figure 5B:
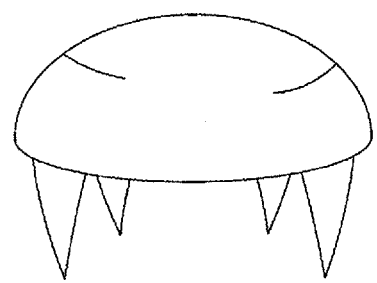

Cap 4 may be tight-fitted to the distal tip of helically wound coil 5. In other embodiments, cap 4 is attached by, for example, adhesive, soldering or welding. FIGS. 5(A) and (B) illustrates two examples of a cap suitable for use with the guide wire. FIG. 5(A) shows a cap having slits near the circumferential edge of the cap and a continuous circumferential wall extending from the top of the cap. This wall can provide for stabilization and securement of the cap to the helically wound coil. FIG. 5(B) shows a cap having a plurality of legs that provide stabilization and securement of the cap to the helically wound coil.

Figure 3A:
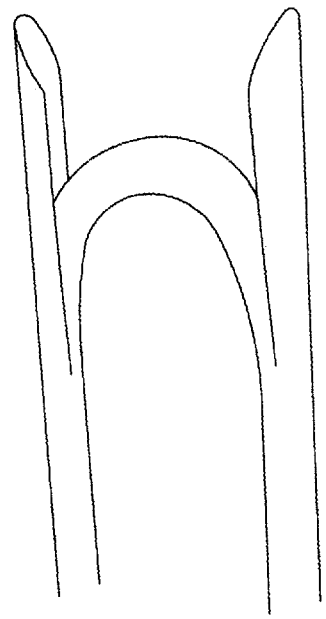
In FIG. 3(A) both blades have a pointed configuration.
Figure 3B:
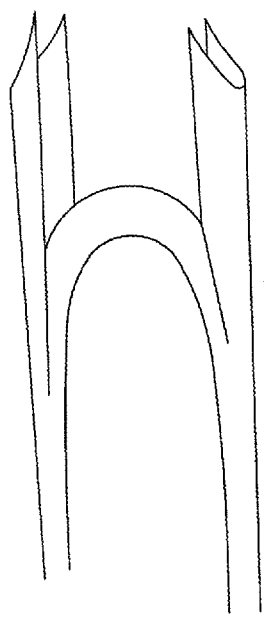
In FIG. 3(B) both blades have a "U" shaped configuration.
Figure 4A:
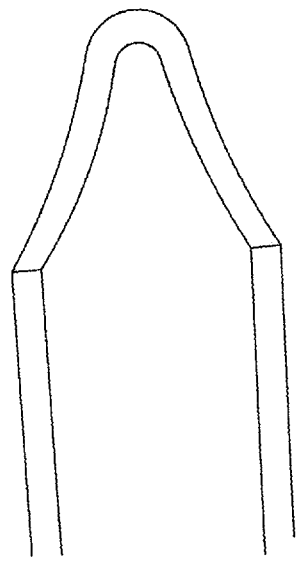
FIGS. 4 (A) and 4(B) are illustrations showing blade regions of the two embodiments illustrated in FIGS. 3(A) and (B) respectively.
Figure 4B:
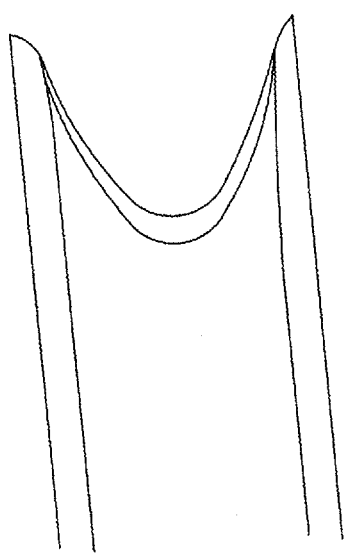

FIGS. 3(A) and (B) shows embodiments of the distal end of deflection wires 2 and 7 and their attached blades 1 and 8 respectively. The blades may extend from a circumferential edge of cap 4, for example through slits. The blades may be attached to the deflection wires in any suitable manner. For example, the blades may be attached by adhesive, soldering or welding. One or both blades may be shaped, for example, in a pointed configuration as illustrated in FIGS. 3(A) and 4(A). Alternatively, one of both blades may be formed, for example, in a "U" shaped configuration as is illustrated in FIGS. 3(B) and 4(B). A plurality of blades may be attached to one of both of the deflection wires. Returning to FIG. 3(A), the distal ends of first deflection wire 2 and second deflection wire 7 may be joined.

Figure 6A:
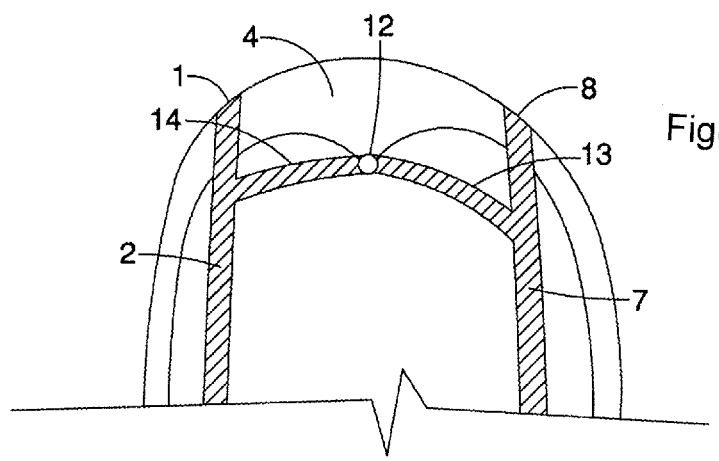
FIG. 6(A) shows the blades retracted.
Figure 6B:
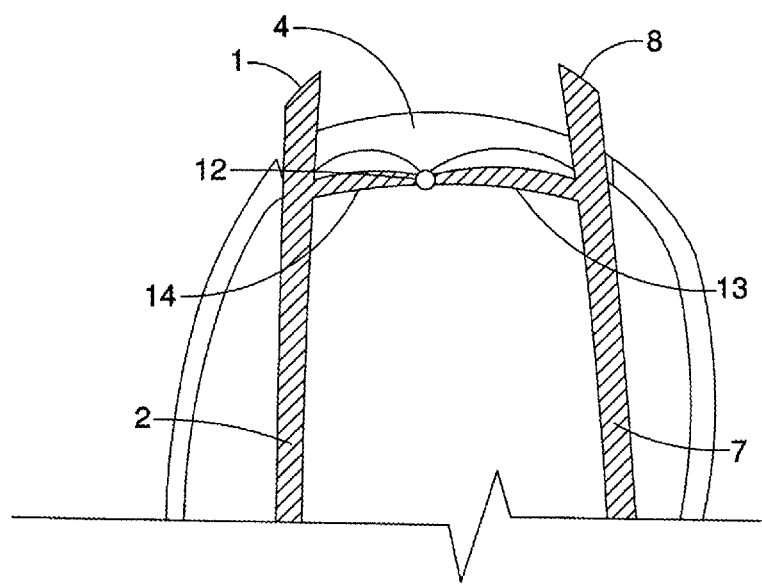
FIG. 6(B) shows the blades extended.

Alternatively, the distal ends of both deflection wires may be attached to the inside of cap 4. FIGS. 6 (A) and (B) illustrates such an embodiment. In FIGS. 6 (A) and (B), blades 1 and 8 are fixed to deflection wires 2 and 7 respectively. The distal end of both deflection wires attach to the interior of cap 4 at cap attachment point 12. FIG. 6(A) shows both blades in a retracted configuration, while in FIG. 6(B) the blades are extended. Extension of blades 1 and 8 is achieved by moving deflection wires 2 and 7 distally. As the blades are extended, portions 13 and 14 of deflection wires 7 and 2, corresponding to those portions of the deflection wires between cap attachment point 12 are the region of attachment of the blades, flex and move distally towards the inside of the distal interior of cap 4.

Figure 2A:
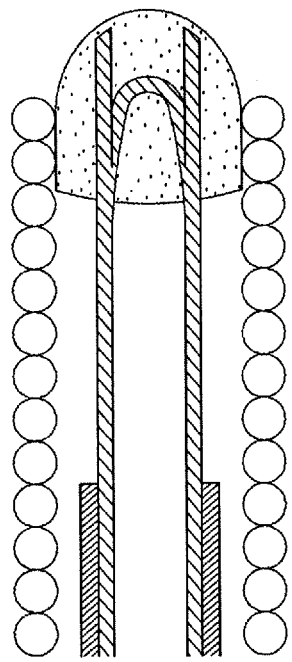
FIGS. 2 (A) and (B) are illustrations showing the embodiment of FIG. 1 with both blades retracted 2(A) or with one blade extended 2(B).
Figure 2B:
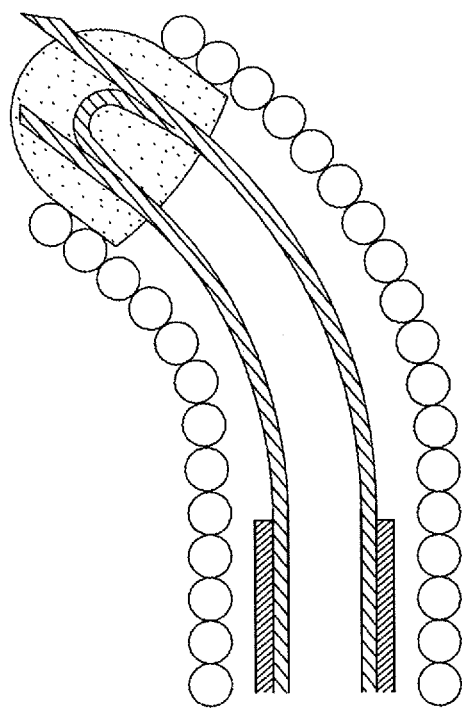

Turning now to FIG. 2, FIG. 2(A) illustrates guide wire 10 aligned to longitudinal movement axis A-A'. In this illustration, blade 1 and blade 8 are in their retracted configuration. In this configuration, the blades may be, for example, flush with an interior surface of cap 4. FIG. 2(B) illustrates guide wire 10 with blade 8 in an extended position while blade 1 is still in its retracted position. The distal tip of helically wound coil 5 is deflected in a direction on an axis perpendicular to the A-A' axis of helically wound coil 5. Such a deflection may result from a distal movement of deflection wire 7 from a relaxed position.

Methods of Use

Another aspect of the present invention provides a method of crossing an occlusion in a lumen of a patient vessel. In one embodiment, the method includes introducing a distal end of an embodiment of a guide wire as disclosed above into the patient vessel. In some embodiments, the guide wire is introduced by a percutaneous access method. The guide wire is advanced until the distal end of the guide wire is positioned at a first side of the occlusion. The guide wire may be positioned with the aid of, for example, tactile feedback or a visualization method such as radiography, ultrasound, or MRI.

The first deflection wire is translationally displaced in a distal direction to deflect the distal end of the helically wound coil towards the vessel wall and to extend the first blade to contact and cut the wall. The second deflection wire may also be displaced to bring the second blade into contact with the vessel wall. The distal end of the guide wire is then further advanced to enter a subintimal layer of the wall of the vessel and through the subintimal region of the wall. If necessary, one or both of the blades can be extended during the passage through the subintimal layer.

The distal end of the guide wire is advanced through the subintimal region in a direction substantially aligned with a path of the vessel and for a distance sufficient to position the distal end of the guide wire adjacent to a region of the vessel beyond the obstruction. At this point, at least one of the deflection wires is translationally displaced to deflect the distal end of the helically wound coil through the vessel wall and into the lumen of the vessel at the other side of the obstruction.

In one embodiment, the vessel is a vascular vessel, for example a vein or artery of the coronary or peripheral vascular system. The peripheral artery may be, for example, an artery of the leg, such as the femoral artery. The obstruction may be a partial or total obstruction and may result from, for example, thrombosis, a blood clot or a buildup of plaque. In other embodiments, the body lumen may, for example, be a passage of the alimentary system, the urogenital system or the biliary system.

Once the obstruction has been by-passed, the path through the subintimal layer may be enlarged. For example, the method may also include advancing a device including a balloon catheter over the guide wire and positioning an expandable balloon portion of the balloon catheter within the subintimal region. The balloon is then expanded within the subinitimal region to expand the pathway circumventing the obstruction. The device may also include an expandable stent positioned on the expandable balloon portion of the balloon catheter. In this embodiment, the stent may provide additional support to prevent collapse of the pathway through the subinitimal region. In other embodiments, a balloon-expandable or a self-expandable stent may be advanced over the guide wire to a position within the subinitimal region and then expanded to enlarge the path.

The expandable balloon and/or stent may be coated with an elutable bioactive agent such as a taxane agent, such as paclitaxel or a derivative thereof; a mammalian target of rapamycin (mTOR) inhibitor such as sirolimus or a derivative thereof such as pimecrolimus, tacrolimus, everolimus, zotarolimus, novolimus, myolimus, temsirolimus, deforolimus, or biolimus. Other bioactive agents that may be present include, but are not limited to, antithrombogenic agents; anti-cancer agents; immunosuppressive agents; anti-inflammatory agents; anti-microbial agents and combinations of the agents listed above.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

I claim:

1. A guide wire comprising:
   a helically wound coil having a proximal end and a closed distal end and a longitudinal movement axis, wherein the distal end of the helically wound coil is closed with a cap; and
   a first deflection wire housed within the helically wound coil and having a proximal end and a distal end, wherein the first deflection wire, responsive to a translational displacement on the longitudinal movement axis in a distal direction, simultaneously acts to deflect the distal end of the helically wound coil in a first direction, the first direction being on an axis perpendicular to the longitudinal movement axis of the helically wound coil, while moving a first blade attaching to a distal portion of the first deflection wire from a retracted position to an extended position, the first blade in the retracted position being housed entirely within the cap and the first blade in the extended position extending from the cap.

2. The guide wire of claim 1, further comprising a second deflection wire housed within the helically wound coil; wherein a distal end of the second deflection wire attaches to the distal end of the first deflection wire, and the second deflection wire, responsive to a translational displacement on the longitudinal movement axis, simultaneously deflects the distal end of the helically wound coil in a second direction, the second direction being opposite the first direction and on an axis perpendicular to the longitudinal movement axis of the helically wound coil, while moving a second blade attached to a distal end of the second deflection wire from a retracted position to an extended position, the second blade in the retracted position housed entirely within the cap and the second blade in the extended position extending distally from the cap.

3. The guide wire of claim 2, further comprising a stability sheath positioned between the deflection wires and the helically wound coil.

4. The guide wire of claim 1, wherein the first blade extends from a circumferential edge of the cap.

5. The guide wire of claim 1, further comprising a longitudinal radiopaque marker line disposed on an exterior surface of the helically wound coil.

6. The guide wire of claim 1, wherein the cap is tight-fitted into the distal tip of the coil to enable movement of the first blade from the retracted position to the extended position.

7. The guide wire of claim 1, wherein the first blade in the retracted position is flush with an interior surface of the cap.

8. The guide wire of claim 1, comprising a plurality of first blades attaching to the distal end of the first deflection wire.

9. The guide wire of claim 1, further comprising a lubricious polymer coating surrounding the helically wound coil.

10. A guide wire comprising:
a helically wound coil having a proximal end and a distal end, wherein coils at the distal end are in a more relaxed state than coils at the proximal end;
a cap secured to the distal end of the helically wound coil;
a first deflection wire and a second deflection wire disposed within the helically wound coil and secured together at the distal end of the helically wound coil, the first deflection wire having a proximal end and a distal end and the second deflection wire having a proximal end and a distal end, wherein the first deflection wire extends from the proximal end of the helically wound coil to the distal end of the helically wound coil; and
a first blade attaching to the distal end of the first deflection wire and a second blade attaching to the distal end of the second deflection wire, the first blade housed within the cap when the first deflection wire is in a relaxed state and the first blade extended from the cap when the first deflection wire is in a deflection state, and the second blade housed within the cap when the second deflection wire is in a relaxed position and the second blade extended from the cap when the second deflection wire is in a deflection state.

11. A method of crossing an occlusion in a lumen of a patient vessel, the method comprising:
introducing a distal end of a guide wire into the patient vessel, wherein the guide wire comprises:
a helically wound coil having a proximal end and a closed distal end and a longitudinal movement axis, wherein the distal end of the helically wound coil is closed with a cap; and
a first deflection wire housed within the helically wound coil and having a proximal end and a distal end, wherein the first deflection wire, responsive to a translational displacement on the longitudinal movement axis in a distal direction, simultaneously acts to deflect the distal end of the helically wound coil in a first direction, the first direction being on an axis perpendicular to the longitudinal movement axis of the helically wound coil, while moving a first blade attaching to a distal portion of the first deflection wire from a retracted position to an extended position, the first blade in the retracted position being housed entirely within the cap and the first blade in the extended position extending distally from the cap; and
a second deflection wire housed within the helically wound coil; wherein a distal end of the second deflection wire attaches to the distal end of the first deflection wire, and the second deflection wire, responsive to a translational displacement on the longitudinal movement axis, simultaneously deflects the distal end of the helically wound coil in a second direction, the second direction being opposite the first direction and on an axis perpendicular to the longitudinal movement axis of the helically wound coil, while moving a second blade attaching to a distal end of the second deflection wire from a retracted position to an extended position, the second blade in the retracted position housed within the cap and the second blade in the extended position extending distally from the cap;
advancing the distal end of the guide wire to a first end of the occlusion;
translationally displacing the first deflection wire, whereby the distal end of the helically wound coil is deflected and the first blade is extended to contact and cut a wall of the vessel;
advancing the distal end of the guide wire to enter a subintimal layer of the wall of the vessel;
advancing the distal end of the guide wire through a subintimal region of the wall of the vessel, wherein the advancing through the subintimal region is in a direction substantially aligned with a path of the vessel and wherein the advancing is sufficient to position the distal end of the guide wire adjacent to a region of the vessel beyond the obstruction;
translationally displacing the first deflection wire or the second deflection wire, whereby the distal end of the helically wound coil is deflected to enter the lumen of the vessel at a second side of the obstruction.

12. The method of claim 11, wherein the vessel is a vascular vessel.

13. The method of claim 12, where the obstruction is a result of thrombosis.

14. The method of claim 11, further comprising:
advancing a device comprising a balloon catheter over the guide wire;
positioning an expandable balloon portion of the balloon catheter within the subintimal region; and
expanding the balloon within the subinitimal region, whereby the subinitimal region is expanded.

15. The method of claim 14, wherein the device further comprises an expandable stent positioned on the expandable balloon portion of the balloon catheter.

16. The method of claim 11, further comprising:
advancing a device comprising an expandable stent over the guide wire;
positioning the expandable stent within the subintimal region; and
expanding the expandable stent within the subinitimal region, whereby the subinitimal region is expanded.

17. The method of claim 16, wherein the expandable stent is a self-expandable stent.

18. The method of claim 16, wherein the expandable stent is a balloon-expandable stent.

19. The method of claim 16, wherein the expandable stent comprises a bioactive agent.

20. The method of claim 14, wherein the expandable balloon portion of the balloon catheter comprises a bioactive agent.

* * * * *